US009711056B1

(12) United States Patent
Nguyen

(10) Patent No.: US 9,711,056 B1
(45) Date of Patent: Jul. 18, 2017

(54) APPARATUS, METHOD, AND SYSTEM OF BUILDING AND PROCESSING PERSONAL EMOTION-BASED COMPUTER READABLE COGNITIVE SENSORY MEMORY AND COGNITIVE INSIGHTS FOR ENHANCING MEMORIZATION AND DECISION MAKING SKILLS

(71) Applicant: FUVI COGNITIVE NETWORK CORP, Framingham, MA (US)

(72) Inventor: Phu-Vinh Nguyen, Massachusetts, MA (US)

(73) Assignee: FUVI COGNITIVE NETWORK CORP., Framingham, MA (US)

( * ) Notice: Subject to any disclaimer, the term of this patent is extended or adjusted under 35 U.S.C. 154(b) by 0 days.

(21) Appl. No.: 15/156,883

(22) Filed: May 17, 2016

Related U.S. Application Data

(60) Provisional application No. 62/308,202, filed on Mar. 14, 2016.

(51) Int. Cl.
| G09B 25/00 | (2006.01) |
| G09B 5/02 | (2006.01) |
| A61B 5/16 | (2006.01) |
| A61B 5/00 | (2006.01) |
| G06K 9/78 | (2006.01) |
| G10L 25/63 | (2013.01) |

(52) U.S. Cl.
CPC .............. *G09B 5/02* (2013.01); *A61B 5/165* (2013.01); *A61B 5/743* (2013.01); *A61B 5/7425* (2013.01); *G06K 9/78* (2013.01); *G10L 25/63* (2013.01); *A61B 2560/0475* (2013.01)

(58) Field of Classification Search
CPC ........... G09B 5/02; A61B 5/165; A61B 5/743; A61B 5/7425; A61B 2560/0475; G06K 9/78; G10L 25/63
See application file for complete search history.

(56) References Cited

U.S. PATENT DOCUMENTS

| 6,190,314 B1 * | 2/2001 | Ark .......................... A61B 5/16 463/36 |
| 7,805,309 B2 | 9/2010 | Carpenter |
| 7,849,034 B2 | 12/2010 | Visel |

(Continued)

FOREIGN PATENT DOCUMENTS

| EP | 2531912 A2 | 12/2012 |
| WO | 2007081307 A1 | 7/2007 |
| WO | 2011/097309 A2 | 8/2011 |

OTHER PUBLICATIONS

Steven Pinker, Thinking Machine, How the Mind Works, 2009, p. 59-148.

(Continued)

*Primary Examiner* — Michael Grant
(74) *Attorney, Agent, or Firm* — Sughrue Mion, PLLC

(57) ABSTRACT

A personal emotion-based cognitive assistant system includes one or more components which may be worn by a user as a headset, one or more sensors that capture an emotional state of the user, a processor that identifies personal meaning of an environment of the user based on the captured emotional state, and a memory that stores the identified personalized meaning with data about the environment in different areas of the memory based on the identified personal meaning.

22 Claims, 9 Drawing Sheets

(56) References Cited

U.S. PATENT DOCUMENTS

| | | | |
|---|---|---|---|
| 8,862,317 | B2 | 10/2014 | Shin et al. |
| 9,101,279 | B2 | 8/2015 | Ritchey et al. |
| 9,171,092 | B2 | 10/2015 | Kruglick |
| 9,177,257 | B2 | 11/2015 | Kozloski et al. |
| 9,355,110 | B1* | 5/2016 | Chi .................... G02B 27/0172 |
| 2002/0029203 | A1 | 3/2002 | Pelland et al. |
| 2002/0032689 | A1* | 3/2002 | Abbott, III ........ G06F 17/30017 |
| 2010/0042567 | A1 | 2/2010 | Visel |
| 2010/0100546 | A1* | 4/2010 | Kohler .............. G06F 17/30017 707/739 |
| 2013/0063550 | A1* | 3/2013 | Ritchey ................ G05D 1/0038 348/36 |
| 2013/0152092 | A1 | 6/2013 | Yadgar |
| 2013/0211238 | A1* | 8/2013 | DeCharms ........... A61B 5/4824 600/418 |
| 2014/0067730 | A1* | 3/2014 | Kozloski ............. G06F 19/3481 706/12 |
| 2014/0347265 | A1 | 11/2014 | Aimone et al. |
| 2014/0351337 | A1* | 11/2014 | Pal ......................... G09B 19/06 709/204 |
| 2015/0052092 | A1* | 2/2015 | Tang .................... G06N 99/002 706/16 |
| 2015/0297108 | A1* | 10/2015 | Chase ...................... G09B 5/00 600/9 |
| 2015/0297109 | A1* | 10/2015 | Garten ............... A61B 5/04845 600/544 |
| 2015/0356151 | A1 | 12/2015 | Sanchez et al. |
| 2016/0042648 | A1* | 2/2016 | Kothuri ................... G06F 3/015 434/236 |
| 2016/0077547 | A1* | 3/2016 | Aimone .................. G06F 3/012 345/8 |
| 2016/0379106 | A1* | 12/2016 | Qi ....................... G06N 99/005 706/11 |

OTHER PUBLICATIONS

Marvin Minsky, 7. Thinking, The Emotion Machine, Commonsense Thinking, Artificial Intelligence, and the Future of the Human Mind, 2006, p. 215-253.

Cyma Van Petten, Chapter 19 Selective Attention, Processing Load, and Semantics: Insights from Human Electrophysiology, Cognitive Electrophysiology of Attention, 2014, p. 236-253.

Varun Bajaj et al., Human Emotion Classification from EEG Signals using Multiwavelet Transform, 2014 International Conference on Medical Biometrics, 2014, p. 125-130.

Choubeila Maaoui et al., Emotion Recognition through Physiological Signals for Human-Machine Communication, Cutting Edge Robotics 2010, Sep. 1, 2010, p. 318-333.

"Steven Pinker on mind as a system of organs of computation", Voices Compassion Education, http://voiceseducation.org/node/6914, Jan. 11, 1997.

Microchip PIC 32NX1XX/2XX 28/36/44-PIN, Microchip Technology Incorporated, 2011-2016, p. 1-344.

Now-Noise, 8-Channel, 24-Bit Analog Front-End for Biopotential Measurements, ADS 1299, Texas Instruments Incorporated, Jul. 2012.

Steven Pinker on How the Mind Works: Cognitive Science, Evolutionary Biology (1997) (https://youtu.be/WfGJGXJ2xtl) Web Based Video Published Dec. 2, 2014.

Learning and Memory: How it Works and When it Fails (https://youtu.be/a_HfSnQqeyY) Web Based Video Published Jun. 8, 2010.

16. Learning: Support Vector Machines (https://youtu.be/_PwhiWxHK8o) Web Based Video Published Jan. 10, 2014.

Machine Learning Made Easy (https://youtu.be/IbNrlwV6Lj4) Web Based Video Published Sep. 18, 2015.

10. Introduction to Learning, Nearest Neighbors (https://youtu.be/09mb78oiPkA) Web Based Video Published Jan. 10, 2014.

OPEN BCI 32 Bit Board Graphic Square, Open BCI, www.openbci,com, last visited Aug. 1, 2016.

International Search Report and Written Opinion, dated Aug. 25, 2016, issue dby the International Searching Authority in counterpart International Patent Application No. PCT/US16/34043.

* cited by examiner

FIGURE 4
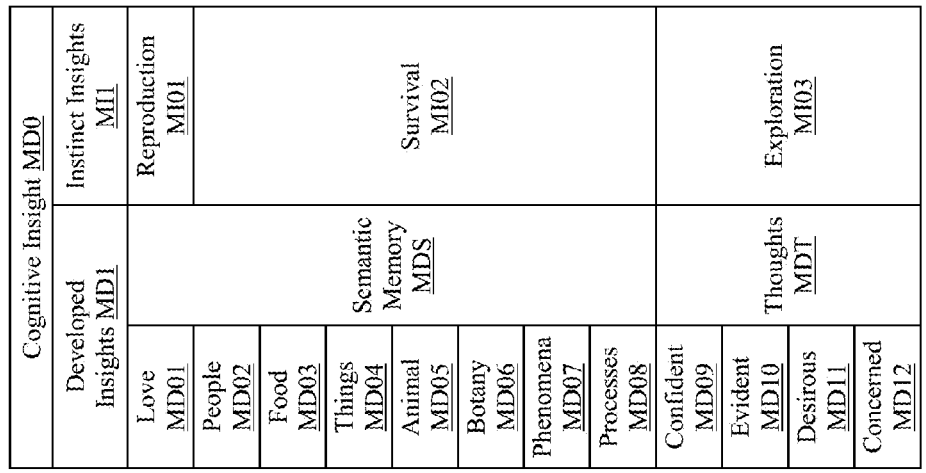
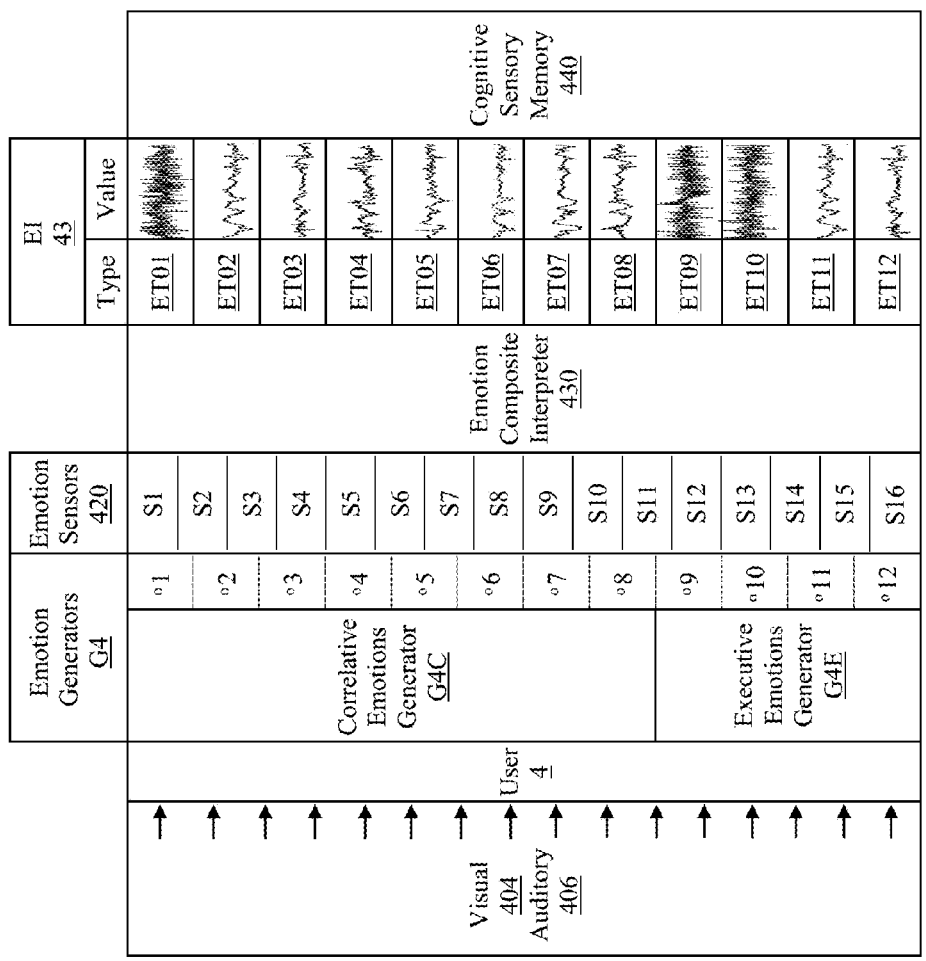

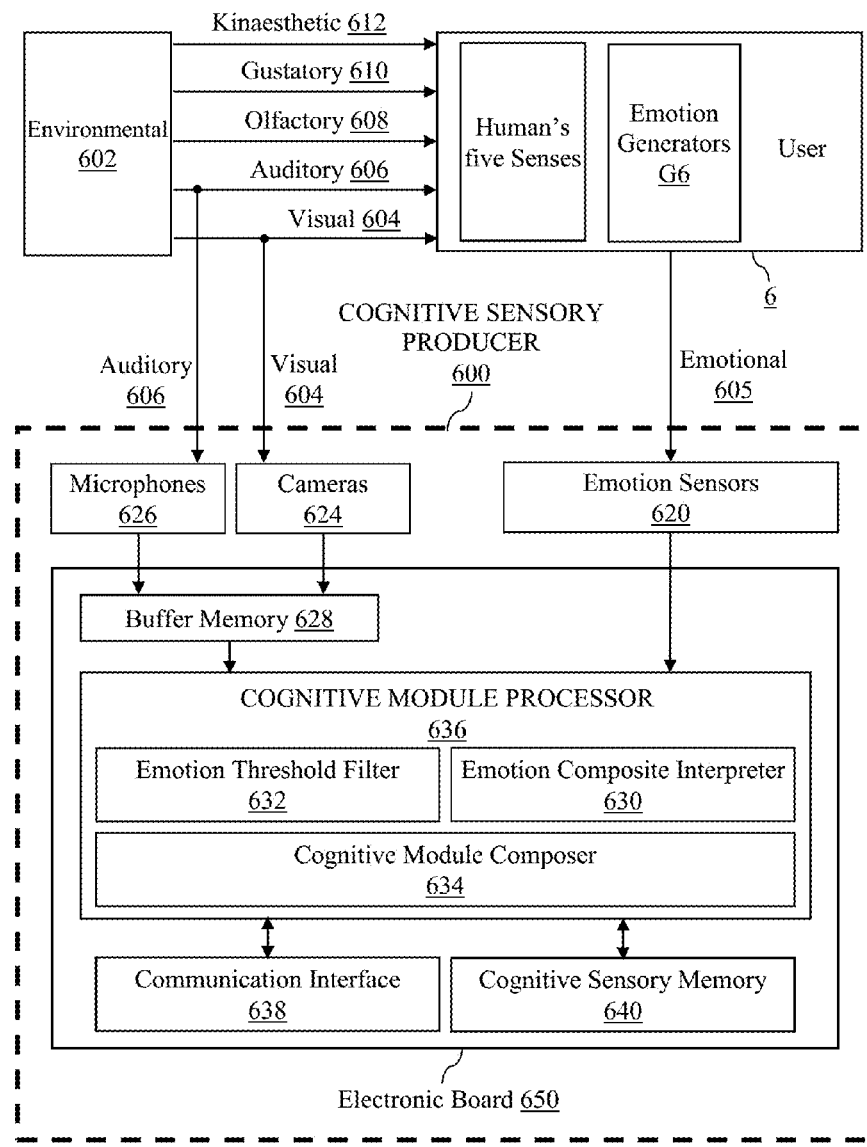

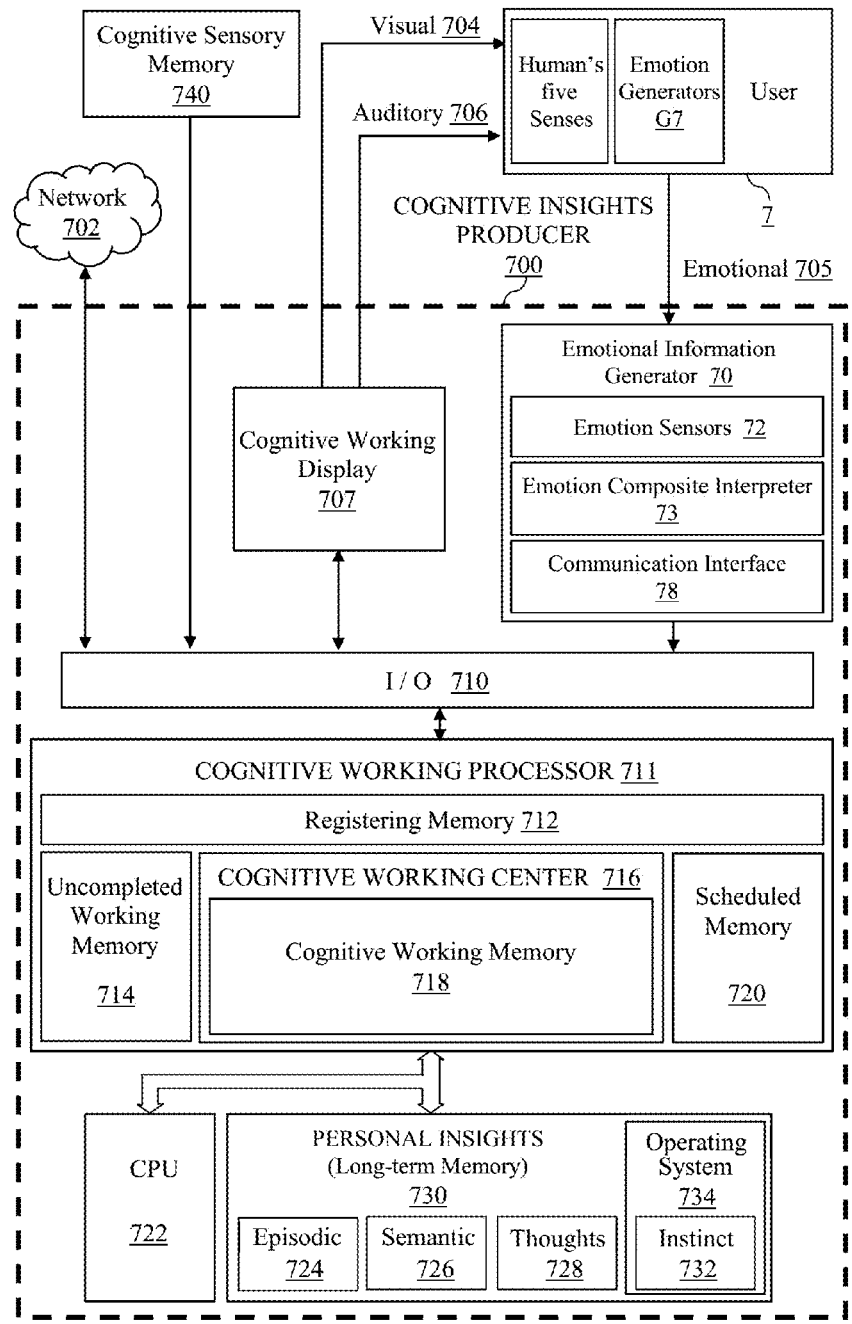

APPARATUS, METHOD, AND SYSTEM OF BUILDING AND PROCESSING PERSONAL EMOTION-BASED COMPUTER READABLE COGNITIVE SENSORY MEMORY AND COGNITIVE INSIGHTS FOR ENHANCING MEMORIZATION AND DECISION MAKING SKILLS

CROSS-REFERENCE TO RELATED APPLICATIONS

This application claims priority from U.S. Provisional Application No. 62/308,202, filed on Mar. 14, 2016, in the U.S. Patent Office, the entire disclosure of which is incorporated herein by reference.

BACKGROUND

1. Field

Apparatuses, methods, systems, and computer readable mediums consistent with exemplary embodiments broadly relate to cognitive technology, and more particularly, to providing emotion-based cognitive sensory memory and cognitive insights.

2. Description of Related Art

Due to numerous advances in technologies including smaller devices, faster processing, and more storage capabilities, its use expands to facilitate user's everyday activities and various other functions. Nowadays, computing devices may take your order in a restaurant and transmit it to the kitchen for implementation. Computing devices may have an automated personal assistant software built into the device e.g., Siri, Google Now, and so on. These automated personal assistants can conduct a dialogue with the user and provide the requested information.

To improve user experience, personal assistants may be situational and context aware see e.g., U.S. Pat. No. 6,190,314. Additionally, personal assistants may build a context database based on user prior interaction see e.g., U.S. Pat. No. 9,171,092.

Additionally, personal assistants have been developed that not only provide information to the user but may also execute some basic tasks. In related art, virtual personal assistants may understand a user's spoken and/or written input, perform task such as roll a dice in a virtual game played by the user, and adapt to user preferences over time, see e.g., U.S. Patent Publication No. 20130152092.

Also, some personal assistants may have personality parameters that can be adjusted based on the device interaction with the user, see e.g., U.S. Patent Publication No. 20020029203 and EP 2531912.

In related art, the user input usually performed via voice communication with a computer or written or touch input drives a personal assistance. Further, the personal assistance provides information and/or performs basic tasks based on this input and based on applied user preferences, which may vary over time, or some sort of contextual awareness.

In related art, personal assistance is very limited and does not account for an intelligence of a human mind. Although some memory enhancement devices are known, see e.g., U.S. Pat. No. 9,101,279 and U.S. Pat. No. 9,177,257, cognitive insights only exist in human's brain and the existing computers are not able to access and use this insight.

Accordingly, there is a need in the art to improve providing cognitive insights that would be personalized based on complexities analogous to human emotions and mind. There is a need in the art to have a computer mimic a brain of an individual to assist the user in daily learning, memorizing, thinking, and making decisions based on his personal insights.

Human thoughts often have an emotional component to them. The systems in the related art neglect to account for this emotional component of human thoughts and insights. There is a need in the art to combine an individual emotional component with a cognitive component for individual or personalized insights.

The systems in the related art focus to account for interpreting meaning of context such as images and voice and store them to profiles, graphs, and so on using complex algorithms. The meaning of context or contextual information, however, differs from person to person. That is, the interpretation of context will vary from person to person. There is a need in the art to combine an individual's meaning of the context which takes place in the form of an emotional component with a cognitive component to generate individual or personalized insights.

SUMMARY

According to exemplary, non-limiting embodiments, cognitive assistant system is provided based on cognitive modules embodying sensory information such as visual and auditory data which is synchronized with emotional information, in real time or on the fly.

According to exemplary, non-limiting embodiments, the emotional information is based on multi-emotion signals, embodying different correlative meanings of visual and auditory sensory information towards user's instinct insights and developed insights.

According to exemplary, non-limiting embodiments, the system may generate unverified cognitive sensory memory based on sensory data combined with individual emotional state of the user.

According to exemplary, non-limiting embodiments, the system may generate personalized insights or long-term memory based on verified cognitive sensory memory combined with user's personalized emotional state when the user reviews, consolidates, rehearses the cognitive sensory modules being displayed.

According to exemplary, non-limiting embodiments, the system may generate personalized thoughts and build up thoughts memory (or long-term memory) or cognitive insights based on the process on cognitive modules being retrieved from developed cognitive insights.

Illustrative, non-limiting embodiments may overcome the above-noted disadvantages and problems in the prior art, and also may have been developed to provide solutions to other disadvantages and problems that were not described above. However, a method, an apparatus, a system, and a computer readable medium that operates according to the teachings of the present disclosure is not necessarily required to overcome any of the particular problems or disadvantages described above. It is understood that one or more exemplary embodiment is not required to overcome the disadvantages described above, and may not overcome any of the problems described above.

According to an aspect of exemplary embodiments, a personal emotion-based cognitive assistant system is provided, which includes: at least one sensor configured to capture an emotional state of a user, a processor configured to identify personal meaning of an environment of the user based on the captured emotional state, and a memory configured to store the identified personalized meaning with data about the environment in different areas of the memory based on the identified personal meaning.

According to yet another aspect of an exemplary embodiment, a method of providing personal emotion-based cognitive assistance is provided, which includes: capturing, by at least one sensor, an emotional state of a user, identifying, by a processor, personal meaning of an environment of the user based on the captured emotional state, storing the identified personalized meaning with data about the environment in different areas of a memory based on the identified personal meaning, and outputting results based on the personal meaning of the data.

According to yet another aspect of an exemplary embodiment, a non-transitory computer readable medium configured to store instructions, which when executed by the processor cause the processor to execute various operations is provided. The operations include: receiving an emotional state of a user captured by at least one sensor, identifying personal meaning of an environment of the user based on the received emotional state, storing the identified personalized meaning with data about the environment in different areas of a memory based on the identified personal meaning, and outputting, on a display, results based on the personal meaning of the data.

According to various exemplary embodiment, a user may readily appreciate topics that require further attention when studying, items to purchase, and so on. According to various exemplary embodiment, personalized thoughts are formed based on environment observed by the user. These personalized thoughts may mimic the thoughts of the user's mind and are output to assist the user in making various kinds of decisions. The output may take various forms including suggestions, warnings, listing of contents, repeating certain data during studying, and so on.

BRIEF DESCRIPTION OF THE DRAWINGS

The accompanying drawings, which are incorporated in and constitute a part of this specification exemplify exemplary embodiments and, together with the description, serve to explain and illustrate exemplary embodiments. Specifically:

FIG. 4 is a view illustrating a diagram table for classifying emotional signals to various types of emotions reflecting the user's emotional correlations of environmental information input towards user's cognitive insights according to an exemplary embodiment.

FIG. 6 is a block diagram illustrative a cognitive sensory producer according to an exemplary embodiment.

FIG. 7 is a block diagram illustrating a cognitive insight producer according to an exemplary embodiment.

DETAILED DESCRIPTION OF EXEMPLARY EMBODIMENTS

Figure 1:
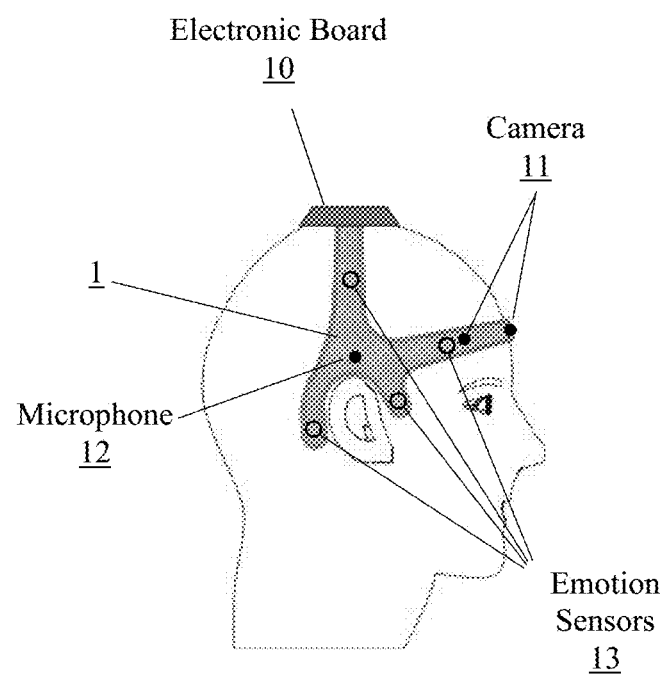
FIG. 1 is a view illustrating a device which captures sensory and emotional data according to an exemplary embodiment.
Figure 2A:
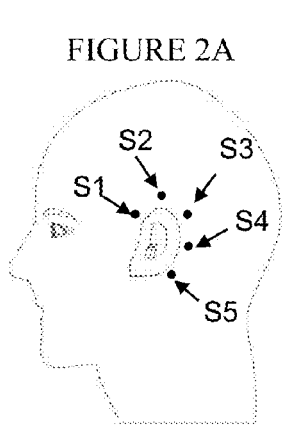
FIGS. 2A-2D are views illustrating emotional sensors to detect emotional information according to an exemplary embodiment.
Figure 2B:
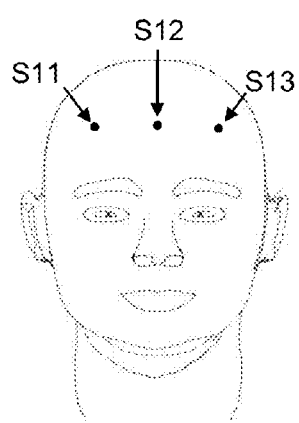
Figure 2C:
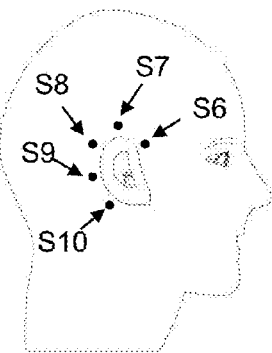
Figure 2D:
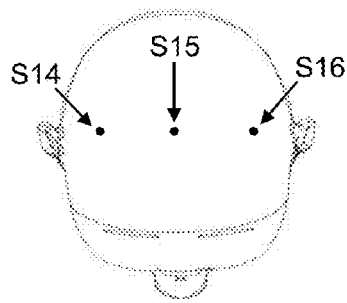

Exemplary embodiments will now be described in detail with reference to the accompanying drawings. Exemplary embodiments may be embodied in many different forms and should not be construed as being limited to the illustrative exemplary embodiments set forth herein. Rather, the exemplary embodiments are provided so that this disclosure will be thorough and complete, and will fully convey the illustrative concept to those skilled in the art. Also, well-known functions or constructions may be omitted to provide a clear and concise description of exemplary embodiments. The claims and their equivalents should be consulted to ascertain the true scope of an inventive concept.

A human mind is a complex intellectual facility that embodies declarative information that can work on working memory and central executive of the brain under visual and auditory forms. The declarative information being retrieved from long-term memory in human's insights under the forms of episodic memory, semantic memory and thoughts memory. Human's insight is built on the core of axiomatic instinct insight. Human instincts is what is naturally installed in insights, what the human is born with such as instincts to breath, suck, cry, and so on. Human instincts are built up gradually with time. For example, as human develops, he learns that mother and father are the closest people, then he or she learns what is a finger, an apple, numbers, addition operation, and so on. New insight elements are built upon previous ones. Human initial instincts are love, survival, and exploration. Human organs generate emotion signals to help identify the meaning of an object to the individual. If an object is known and meaningful, the emotion signal such as "like", "love", "fear" may be generated. If an object is unknown but catches a person's attention, emotions which belong to an "explorative instinct" such as curious, impressive, attentive may be generated. Human insights causes to generate emotional signals to control the insight building process.

The insight building process begins with human's five senses. Human senses the surrounding environment via sensory information, which includes: visual, auditory, olfactory, kinesthetic, and gustatory information. However, the mind only receives meaningful information that causes at specific places in the human's brain to generate an emotional signal that its value is greater than a threshold value. In mind, the composite visual, auditory, and other sensory inputs in combination with the synchronous composite emotions become the cognitive modules which are classified and stored in different memory domains of the brain, building the cognitive insights of an individual. The cognitive insights, thereof, are the personal, meaningful and well-organized database, ready for every cognitive operations such as thinking, making decisions, and taking actions.

To date, such cognitive insights only exist in human's brains under the complex organs of neurons, hormones, and neurotransmitters that the existing computers are not able to access and use. Even though, existing computers are fast with a large storage capacity, it is still not available to assist the user in daily personal cognitive operations. In related art, computers are incapable of in response to receiving same input as a human user, summarizing and displaying to the user remarkable elements and observations after an event or a user's shopping tour through a big shopping mall. Related art is incapable of accounting for emotional signals and often times composite emotional signals that are built in to human observation of the events. Although an objective informational database may be formed, it is void of the individualized insights of the user.

In an exemplary embodiment, a computer system imitates the workings of a human mind and includes a personalized database such as the one in the user's mind to assist the user in daily learning, memorizing, thinking, and making decisions. In related art, the objective informational database may include information such as 2+3=5 but it is void of user's confidence level with respect to this information. In an exemplary embodiment, the system will not only store that 2+3=5 but also include how comfortable or confident the user is with solving this equation.

In an exemplary embodiment, as detailed below, "2" is a semantic module, stored as emotional photos and stories such as 2 fingers, 2 apples, farther and mother together is two, depending on user's individual history with respect to the number 2. When all cognitive elements on the background of topic are known, the user is confident. In this example, the topic may be addition, and the semantics are numbers 2, 3, 5 and so on. When the correlation of all cognitive element are experienced: two fingers on a hand and/or two apples and three fingers on a hand and/or three apples with total of five fingers on a hand or five apples in a bowl, the user feel confident or the user's confidence level is high. The process of "addition" learning is completed and the human has built a new semantic module in his insights. The new semantic insight is built and stored in both user's brain and the system. The system is driver by user's emotion. The system does not forget what is saved in its insights unlike a human and helps people enhance their abilities of memorizing.

Additionally, in an exemplary embodiment, the user may have different feelings about the operations such as addition and subtraction, the system will account for these differences. In related art, computer will treat "add" and "subtract", "gain" and "loose" in the same way but providing them with the same cognitive meaning. In an exemplary embodiment, the system may observe that the user likes to gain and does not like to lose. The user likes to have more chocolates, more toys, and so on. While the user may not like to lose a toy or a candy, and so on. Accordingly, in an exemplary embodiment, the system will account for these differences and similar to a human mind, the operations "add", "subtract", "gain", and "loose" will be treated differently. In an exemplary embodiment, the system may provide the processing emotion-based information being retrieved from insights that tends the user's decisions to gain and avoid to lose.

In an exemplary embodiment, cognitive insights are formed by combining cognitive sensory memory with verifying emotional signals received from the user. Accordingly, if the user is studying for an exam, the system may assist the user in determining concepts that require further studying or the ones that the user is having difficulties with. If the user is shopping at the mall, the system may assist the user automatically in capturing photos items he or she liked along the tour then at the end, display them, review and select the most interesting ones In an exemplary embodiment, an emotion-based cognitive system includes an operating system and apparatuses for building and processing cognitive information modules embodying visual information (VI), auditory information (AI), and emotional information (EI). A system, according to an exemplary embodiment, includes at least one camera and one microphone to capture images, videos, voices and sounds that the user views and hears synchronously, and at least one sensor, and preferably more, to capture emotion signals generated from user's brain such as: love, like, curious, attentive, confident, and other different types of emotion signals that correspond to the visual and audio inputs, as described in greater detail below. The system uses threshold values of environmental sensory emotion signals to control filtering process which enables meaningful visual information and auditory information from the environment link to inside. In an exemplary embodiment, the system captures the thoughtful emotion signals generated when the user turns his (or her) mind to a working memory, the system uses thoughtful emotion signals to switch off environmental information input, e.g., visual and auditory from cameras and microphones to avoid unsynchronized or improperly synchronized composition. In this instance, emotion relates to a recent thought in the user's mind and not related to what the user sees and hears although the emotion value is above a threshold. If the system allows this type of input, it will lead to mis-composition.

In an exemplary embodiment, the system may include a processing apparatus configured to compose cognitive information modules embodying environmental filtered sensory visual and auditory information and the synchronized emotional information. In an exemplary embodiment, the system may include a non-transitory computer readable storage medium for storing the cognitive sensory information modules building cognitive sensory memory.

In an exemplary embodiment, a cognitive processing system configured to produce cognitive insights includes a central processing unit (CPU), a cognitive working processor, a long-term memory, and an emotion information generator, and a cognitive working display. The long term memory according to an exemplary embodiment may include an episodic memory, a semantic memory, and a thoughts memory. The cognitive working processor includes cognitive working center, a registering memory such as a buffer, an uncompleted working memory and a scheduled memory, which are explained in greater detail below. Additionally, in an exemplary embodiment, emotion-based operating instructions may be generated based on the human instinct insights, as explained in greater detail below.

FIG. 1 is a view illustrating a device which captures sensory and emotional data according to an exemplary embodiment.

As shown in FIG. 1, cameras 11 may be provided on a headset 1 according to an exemplary embodiment. That is, a left camera, a central camera, and a right camera (not shown) may be provided to capture visual data according to an exemplary embodiment. This is provided by way of an example and not by way of a limitation. One of ordinary skill in the art would readily appreciate that visual data may be captured with a personal device such as a user's personal data assistant or a cellular telephone. Additionally, one of ordinary skill in the art would readily appreciate that any number of cameras may be used and that the visual data may be provided by a single camera or by a plurality of cameras. The captured visual data (VI) may then be transferred to an electronic board 10, which includes at least a memory coupled with a processor (not shown).

In an exemplary embodiment, the electronic board 10 may process sensory information and emotional information to generate cognitive sensory memories, as described in detail below with respect to FIG. 4. In yet another exemplary embodiment, the generated cognitive sensory information may be transmitted to another remote device for storage, monitoring or further processing via a communication interface (not shown) provided on the headset 1. For example, the headset 1 may include a communication interface (e.g., a network card, an antenna, and other interfaces known to one of ordinary skill in the art or later developed) to transmit the data wirelessly e.g., a Bluetooth, Infrared, WiFi, and/or a cellular network to a remote server or a cloud for further storage, processing or monitoring and co-supervising. For example, a policeman may wear the headset 1 during an investigation and a supervisor can review his work in the office by having the headset 1 transmit policeman's cognitive insights to the supervisor.

Additionally, the headset 1 may include one or more microphones 12 and a battery (not shown). The microphone 12 may include a left ear microphone, a right ear microphone, and a central microphone, by way of an example and not by way of a limitation. One of ordinary skill in the art would readily appreciate that auditory information may be captured via a single microphone or a plurality of microphones.

In an exemplary embodiment, one or more emotional sensors 13 are further provided on a headset 1. While FIG. 1 depicts four emotional sensors, this is provided by way of an example and not by way of a limitation. One of ordinary skill in the art would readily appreciate that a single emotional sensor but preferably multiple emotional sensors are provided to capture emotional information. The emotional sensors 13 detect emotional information (EI). That is, in an exemplary embodiment, emotional information (EI) is obtained from multiple sensors 13 by detecting activities in various parts of the brain. That is, EEG frequency and amplitude change based on user's emotional level. In an exemplary embodiment, inactivity means that the frequency and amplitude of all the EEG components are below a predetermined threshold value. EEG is provided by way of an example and not by way of a limitation.

By way of an example, a human brain outputs low activity signals while the user is relaxing and not concentrating. In other words, low activity signals indicate that the user is not alert, interested, or impressed by his sensory environment. When the user is interested or is paying attention with respect to what is being observed (e.g., heard and seen), the frequency and amplitude of emotion signal change accordingly. If the change is over a predetermined threshold value, it will trigger a gate to enable VI, AI, and EI input to the processor (and/or microprocessor) being embodied in electronic board 10 for processing/composing/generating cognitive sensory modules. This is provided by way of an example and not by way of a limitation. Emotional sensors 13 are explained in greater detail below with reference to FIGS. 2A-2D, according to an exemplary embodiment. The gathered visual information (VI) and audio information (AI) and emotional information are synchronized or linked with each other and are stored in a memory of the electronic board 10.

FIGS. 2A-2D are views illustrating emotional sensors to detect emotional information (EI) according to an exemplary embodiment.

As shown in FIG. 2A, 2C, 2B, 2D, the emotional information (EI) may be obtained based on output from sensors S1-S16, in which at least one sensor may be a reference sensor. In an exemplary embodiment, S1-S16 are EEG sensors that generate a number of channels of band data signals, respectively. That is, S1-S16 detected EEG signal that are being interpreted to respective channel signals ET01-ET12, as detailed below with respect to FIG. 3. FIGS. 2A-2D illustrate positioning of the sensors S1-S16. For example, sensors S1-S10 are placed around the left and right temporal lobe of the brain of the user, which relate to correlative emotions, as explained in greater detail below and sensors S11-S16 are placed around the frontal lobe which relates to executive emotions. In an exemplary embodiment, signals detected by S1-S16 may be used for analyzing, processing based on multiwavelet transform to classify human emotions, inferring signals from a number of specific points being spatially located inside the brain which generate specific types of emotion signal.

Figure 3:
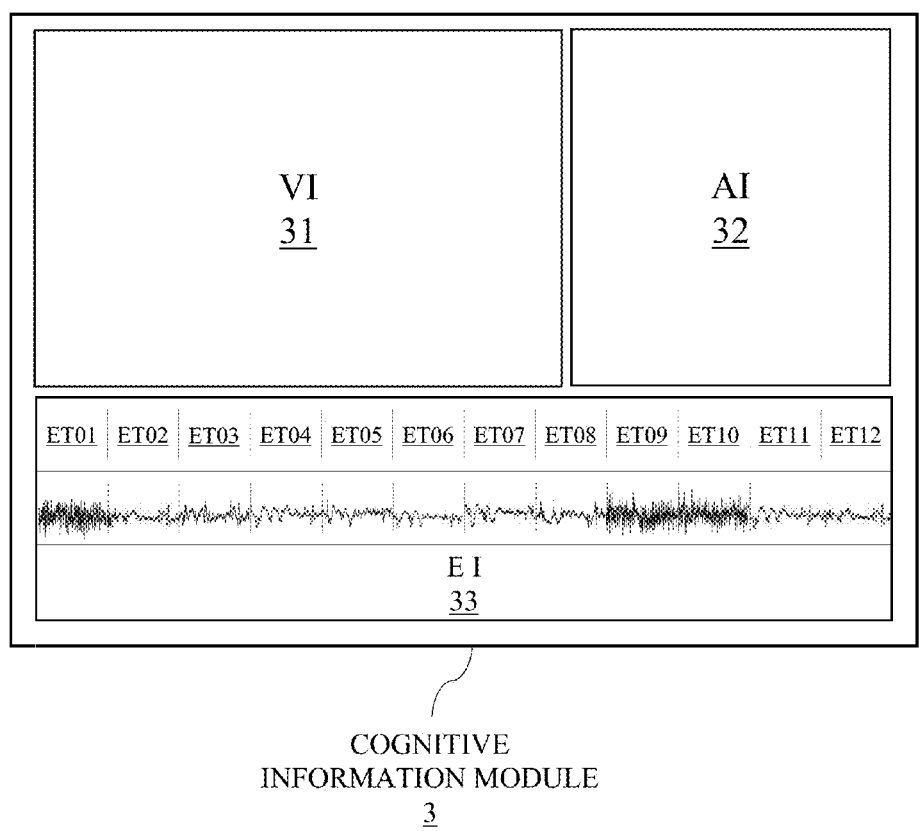
FIG. 3 is a view illustrating components of a cognitive module according to an exemplary embodiment.

FIG. 3 is a view illustrating components of a cognitive module including visual information, auditory information, and emotional information, according to an exemplary embodiment. As shown in FIG. 3, emotional information, which may embody various combinations multi components ET01 to ET12 interpreting different emotional meanings towards user's personal perspectives. In an exemplary embodiment, ET01 to ET12 may generated by processing signals output from the sensors S1-S16. As shown in FIG. 3, the cognitive information module 3 includes VI information 31, AI information 32, and EI information 33. The EI information 33 includes values of the generated emotions ET01-ET12, which are obtained by processing and analyzing outputs from the sensors S1-S16. This is provided by way of an example and not by way of a limitation.

In an exemplary embodiment, FIG. 3 illustrates an interpreted emotional signal when a user meets and hears his loved one. For example, ET01 may indicate the love emotion domain, which is shown as high, ET09 may indicate the confident emotion domain, which is also high, and ET10 may be assigned to evident emotion domain and is also high. When one of ET01-ET08 are high, ET09 and/or ET10 will also be high because a user cannot like something if it is unknown and the user feels lack of confidence with respect to this item. When a user sees his favorite pizza in a new restaurant, he may like it (ET03 will be high and ET10). Also, because it is his favorite food, he feels evident. However, the user may be unsure if this pizza is good at this new restaurant and his ET09 maybe high next time he sees the pizza in this restaurant provided it was good at a current time.

FIG. 4 is a view illustrating a table for classifying emotional signals to various types of emotions reflecting the user's emotional correlations of environmental information input towards user's cognitive insights according to an exemplary embodiment. As shown in FIG. 4, ET01 relate to reproduction when human seeing and/or hearing something relates to this domain, specific point 01, for example, at limbic system (inside the temporal lobe) will generate hormones to induce sexual behavior. Emotional signal from this particular location of the human brain is generated with a specific frequency and amplitude depending on what human sees. The signal is captured by all 16 sensors (by way of an example only and not by way of a limitation), then the processor analyzes the signal, calculates, and defines (based on defined positions of the 16 sensors on the user's head with a support vector machine method) that the signal from point 01 with its original form showed in FIG. 3, by way of an example. The processor also may also determine that ET09 and ET10 correspond to points 09 and 10 in the frontal lobe.

Figure 5A:
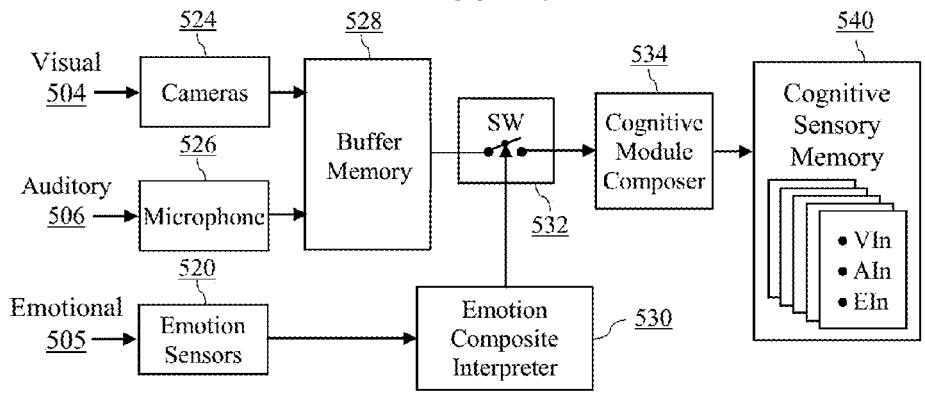
FIGS. 5A and 5B is a flow diagram and a flow chart, respectively, illustrating storing of a cognitive module in a cognitive sensory memory according to an exemplary embodiment.

FIG. 5A is a flow diagram illustrating building a cognitive sensory memory according to an exemplary embodiment. In FIG. 5A, visual information (VI), audio information (AI), and emotional information (EI) are received from cameras 524, microphones 526, and emotional sensors 520, respectively. The VI and AI are continuous streams, which are buffered for long enough to correspond to a delay time of detecting emotional activity. For example, a child can remember what his mother said five second before he is alerted or warned. Based on the emotional information from the sensors 520, an emotion 505 is obtained, analyzed, transformed, and composited in an emotion composite interpreter 530, which is implemented on a processor and/or microprocessor such as the processor in the electronic board 10. As explained above, an emotion may be a composite emotional information, which is obtained based on a number of signals detected by the emotional sensors such as the ones described above. The multiwavelet emotional signal may be broken and composed into various types of emotions, as discussed above. That is, in an exemplary embodiment the emotion signal undergoes a decomposition process. If at least one of the components of the composite emotion is above a threshold value, e.g., the user is paying attention and/or showing interest in what he or she sees or hears, the switch 532 is turned on and the visual information and the audio information, which is stored in a buffer memory 528 are combined with the composite emotion provided by the emotion composite interpreted 530 in a cognitive module composer 534, which may be implemented on a processor or a microprocessor and are stored together in a cognitive sensory memory 540 as a sensory cognitive module. In an exemplary embodiment, a sensory cognitive module comprises VI, AI, and EI formed in a cognitive sensory memory 540.

Figure 5B:
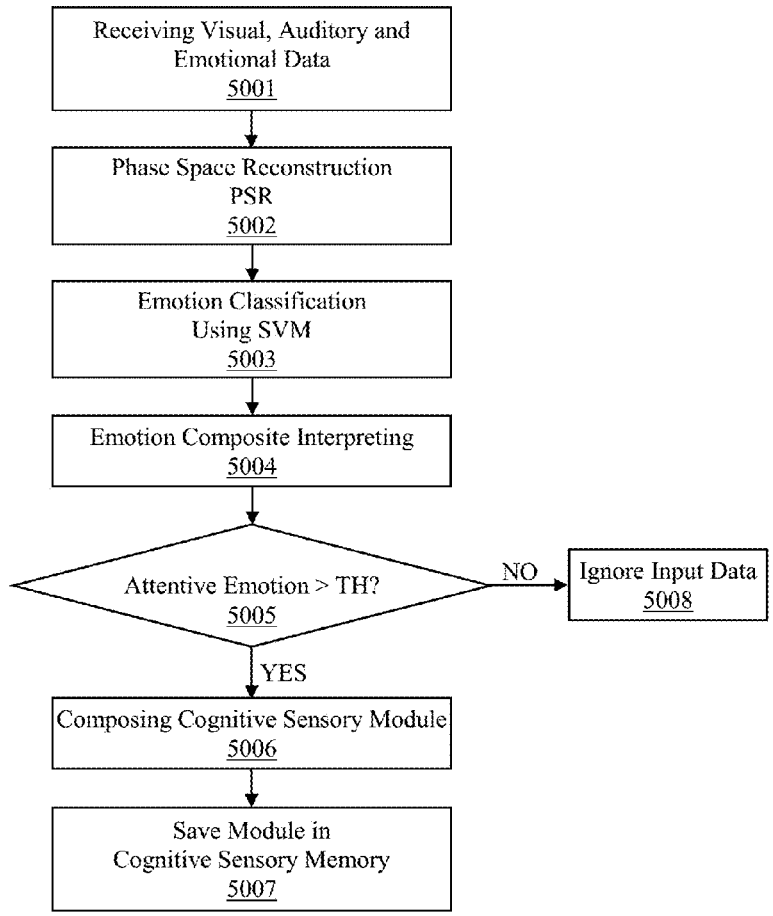

FIG. 5B is a flow chart illustrating a method of building a cognitive sensory memory or module according to an exemplary embodiment. As shown in FIG. 5B, the cognitive system receives visual, audio, and emotional data in operation 5001, for example using headset 1 described above with reference to FIG. 1. In operation 5002, emotion phase space reconstruction PSR occurs based on received emotional data from emotional sensors. In operation 5003, the emotion are classified using support vector machine (SVM). That is, in an exemplary embodiment, emotional data is processed to generate signals ET01-ET12. In operation 5004, the emotion composite interpreting determines values of the components of the generated signals ET01-ET12. In operation 5005, the attentive emotion value is compared to a threshold value, if the attentive emotion value does not exceed above the threshold value in operation 5005, the input data is ignored in operation 5008. Otherwise, in operation 5006, a cognitive sensory module or memory is formed comprising the input data and in operation 5007, the composed cognitive sensory module is stored in cognitive sensory memory.

FIG. 6 is a block diagram illustrating a cognitive sensory producer according to an exemplary embodiment.

According to an exemplary embodiment and as shown in FIG. 6, a user 601 interacts with an environment 602. Interaction with an environment 602 may provide the user 601 with kinesthetic input 612, gustatory input 610, olfactory input 608, auditory input 606, and visual input 604. For example, the user may be sitting at a table in a restaurant, his mind may then receive one or more of various inputs. For example, the user may observe that a waiter is approaching carrying a good looking dish full of spaghetti and places the dish on a table in front of him. The waiter may say "your spaghetti, Sir!" This is provided by way of an example only and not by way of a limitation. A number of other sensory information may be obtained by the user including the food on his plate tastes good (gustatory input) and that it smells good (olfactory input), the user may further observe that the plate is dirty (visual input) and that the plate and/or food is hot (kinesthetic input), and the user may further notice the sizzling sound (auditory input) coming from the plate. In other words, in an exemplary embodiment, interaction with the environment 602 provides the user 601 with various sensory inputs that are being processed by his mind in real-time. The various sensory inputs provided to the user's brain generate an emotional signal. For example, the user may feel that he likes the food. The sensors will detect increased EEG activity, and the composition emotion ET03 may have a very high value, as depicted in FIG. 6 with an emotion generator. This high-value emotional signal enables the system to record all real-time visual, auditory, and emotional information, as described above, to its sensory memory. Later, as described in greater detail below with reference to FIG. 7, the sensory memory or module will be transfer to insights producer to be verified and saved in a user's semantic "spaghetti" domain. Therefore, in user's insights, the semantic "spaghetti" is radically personalized and this information is very meaningful for the user when it is retrieved for topics, thoughts, and so on related to "spaghetti".

In an exemplary embodiment, a user may be wearing a device such as the headset 1, depicted in FIG. 1, this device may be an exemplary cognitive sensory producer 600.

In yet another exemplary embodiment, a cognitive sensory producer may supply cognitive information for computers, personal assistant devices, mobile devices such as cellular telephones. These are provided by way of an example and not by way of a limitation. Although an exemplary embodiment describes the cognitive sensory producer 600 being worn by a user, this is provided by way of an example one. One of ordinary skill in the art would readily recognize that the cognitive sensory producer may be a combination of various apparatuses e.g., external microphones and external cameras, and remote emotional sensors that observe the user, and so on.

According to an exemplary embodiment, the cognitive sensory producer 600 includes at least a processor 636 and a buffer memory 628 which is implemented on a hardware memory, and optionally, a communication interface 638.

In an exemplary embodiment, the cognitive sensory producer 600 includes a number of hardware components and software components such as a hardware memory, a hardware processor, a microphone, a camera, pressure sensors, and so on.

In an exemplary embodiment, unlike personal assistants of the related art, a cognitive assistant operates on at least three sensory inputs i.e., visual information, audio information obtained from the user's environment, and also the emotional information obtained from the user. In an exemplary embodiment, user's cognitive world is integrated with his emotional world. Memories also include user's personal emotions with respect to the cognitive data.

As shown in FIG. 6, the cognitive sensory producer 600 may include cameras 624 which captures user's observations e.g., text written by the professor on a blackboard, a t-shirt displayed in a store windows, and so on. The cognitive sensory producer 600 may further include a microphone 626 to capture user utterance or audio input such as a voice from the viewed target. For example, a professor's voice while he is drawing a graph on a blackboard or explaining a concept depicted on a screen, or an advertising music from a store window, and so on.

In an exemplary embodiment, the cognitive sensory produced 600 captures visual information (VI) via cameras 624, audio information (AI) via the microphones 626 and stores the captured information in a buffer memory 628. The buffer memory 628 may be considered sensory registers of a human mind. For example, a visual sensory register of the buffer memory 628 may store about one second of VI and an auditory sensory register may store about five seconds of AI. This sensory data or information are stored in the various sensory registers of the buffer memory 628 even when the user may not necessarily be paying attention. It is simply the last observation of the user. In other words, it is what happened a predetermined portion of time (e.g., a few seconds) before the emotional signal was obtained. In an exemplary embodiment, one second of the visual information and five seconds of audio information prior to the received emotional information is used. In an exemplary embodiment, this mimics a human brain which responds approximately to one second of visual data and five seconds of audio. This is provided by way of an example and not by way of a limitation. As a variation, the amount of sensory data obtained before the emotional signal is received may be varied based on age, by way of an example. As new data is obtained from the cameras 624 and microphones 626, it overwrites the sensory data currently stored in the buffer 628.

The emotional information or data (EI) obtained from the emotion sensors 620 is input into the cognitive module processor 636. In the cognitive module processor 636, the received emotional data from the emotion sensors 620 is first processed to generate emotional information by the emotion composite interpreter 630. In an exemplary embodiment, emotional data received from various sensors are compared to reference values to obtain types of emotional information and a composite emotion comprising various types of emotions are generated with their corresponding values. Next, a peak of the frequency or width of the amplitude or a combination of the two for each emotion type is compared to a threshold value. In an exemplary embodiment, EI is compared to a threshold value by the emotion threshold filter 632 to detect brain activity or an emotion of a user. In an exemplary embodiment, high emotion indicates meaningful information to the user, which should be stored. Accordingly, in an exemplary embodiment, the emotion threshold filter 632 detects meaningful informational inputs specific to the user. For example, if a user is paying attention, interested in, likes, loves the information about an object being observed, it will be stored in a cognitive sensory memory 640 and may be output by a communication interface 638. As such, the detected emotional signal serves as a trigger to process sensory data in the buffer memory to formulate a cognitive sensory module which are meaningful to the user.

The cognitive sensory module is stored in the cognitive sensory memory 640 until the memory capacity is full and needs to be deleted or is backed up to a separate device, through communication interface 638, for example. Although the communication interface 638 is depicted as part of the cognitive module processor 636, one of ordinary skill in the art would readily appreciate that the communication interface 638 may be a separate component, a combination of hardware and software such as a network card, according to an exemplary embodiment. In an exemplary embodiment, the buffer memory 628 and the cognitive module processor 636 are implemented on an electronic board 650.

Important information may be committed to a long term memory of a user's mind, as described in greater detail with respect to FIG. 7. To commit information to a long term memory, the user needs to rehearse, force him or herself, to memorize the sensory data so that it is stored in the long term memory. It may not be enough to simply pay attention to or like the sensory data but requires additional efforts or work by the user to store information in the long term memory of his brain. In an exemplary embodiment, the short term memories are committed to a long term memory provided they are verified e.g., the level of interest or understanding is re-measured. That is, while cognitive sensory memories stored in the short term area of the memory may change as new memories are received. These cognitive sensory memories may be moved to being stored in a long term memory, as detailed below.

In an exemplary embodiment, based on values output by sensors S1-S12, it may be determined that the user is taking additional efforts to remember the information and similar to the human mind, the information may be committed to a long term memory, as described with reference to FIG. 7.

FIG. 7 is a block diagram illustrating illustrate a cognitive insights producer 700 configured to produce cognitive insights according to an exemplary embodiment. The cognitive insight producer includes a CPU 722, a cognitive working processor 711, a long-term memory 730, an emotion information generator 70, and a cognitive working display 707. The long term memory 730, according to an exemplary embodiment, may include episodic memory 724, semantic memory 726, and thoughts memory 728. The cognitive working processor 711 includes a cognitive working center 716, a registering memory 712, an uncompleted working memory 714, and a scheduled memory 720. The cognitive insights producer 700 includes an emotional information generator 70, which receives emotional input 705 from a user 7.

In an exemplary embodiment, the cognitive insights producer 700 does not work with visual and audio data from cameras and microphones but instead it works with existing visual and audio information provided in the system and displayed on the cognitive working display 707. The emotional information EI is produced by an EI generator 70, in the same way as sensory producer 600 does. When using sensory producer 600 shown in FIG. 6, the user receive VI and AI from the environment to generate EI, while at the producer 700, the user looks into a screen and listens to speakers to generate EI. The cognitive working display 707 displays data from the cognitive working memory 718.

Specifically, in an exemplary embodiment, the user 7 views a cognitive working display 707, which provides the user 7 with visual data 704 and auditory data 706. Based on the user's observation of the environment, emotion generators G7 generates emotions 705. The cognitive insights producer receives the emotional data 705 by an emotional information generator 70 and generates emotional information (EI).

According to an exemplary embodiment, the emotional information generator 70 includes emotion sensors 72 to detect emotions of the user. One of ordinary skill in the art would readily appreciate that this is provided by way of an example and not by way of a limitation. Emotion sensors 72 may be external to the cognitive insights producer 700. Next, the emotional information generator 70 further includes an emotion composite interpreter 73, which processes signals output by emotion sensors 72 and generates various types of emotional information.

Figure 8:
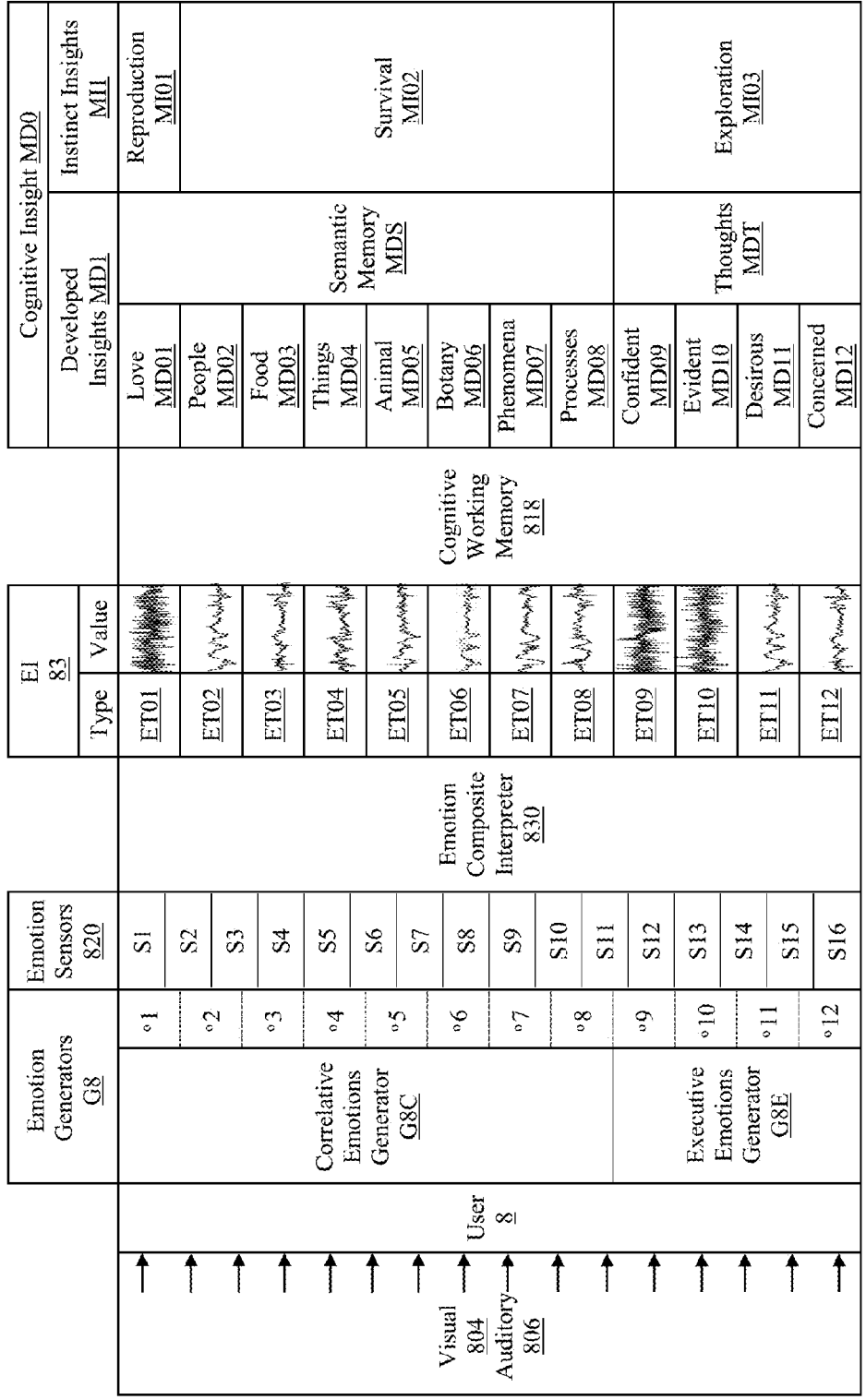
FIG. 8 is a view illustrating a diagram table for classifying emotional signals to various types of emotions reflecting the user's emotional correlations of cognitive working information and user's cognitive insights according to an exemplary embodiment.

FIG. 8 is a view illustrating a diagram table for classifying emotional signals to various types of emotions reflecting the emotional correlations of cognitive working information and user's cognitive insights according to an exemplary embodiment. As shown in FIG. 8, emotions generators G8 of a user 8 generates various emotions such as correlative emotions and executive emotions, which are sensed by the emotion sensors 820 (analogous to the emotion sensors 72). The emotion composite interpreter 73 (depicted as emotion composite interpreter 830 in FIG. 8) analyzes input from the sensors and generates emotional information (EI) 83 comprising ET01 . . . ET12 with corresponding values, by way of an example.

As shown in FIG. 7, the emotion information generator 70 has a communication interface 78, which transmits the generated emotion information (EI 83) to an input and output interface 710, which in turn provides the generated emotion information (EI 83) to a cognitive working processor 711. The generated emotion information may be stored in the registering memory 712.

As shown in FIG. 7, a cognitive sensory module (which may include visual and auditory information combined with the EI) may be registered in a registering memory 712 and then verified or re-classified by the cognitive working memory 718 inside the cognitive working center 716 based on user's emotions on its display on the cognitive working display 705 and its correlative information in the long term memory, as detailed below.

A human brain includes a working memory, which can keep short-term memory received directly from eyes and ears together with related information or data being retrieved from a long term memory, as required, to perform mental operations. For example, to perform the operation of 2+3, the human brain will obtain visual information of 2 and 3 and + from a blackboard to a working memory directly. The semantic meaning of 2, 3, and + needs to be retrieved from the long term memory as visual of the text "two", 2 fingers, two apples, text "three", 3 fingers, three apples, text "adding", father and mother, together, and so on. The human mind of a 5 years old boy, as an example, can draw all these semantics on paper as a cognitive working display. Then, the semantic 5 will be retrieved in his working memory and he can write the answer 5 on a piece of paper.

In an exemplary embodiment, to mimic a human mind, a cognitive working center 716 (which is executed by a hardware processor) is provided, which obtains memories registered in the registering memory 710 and then displays them on a cognitive working display 707 and verifies them based on updated emotional information gathered with updated correlations obtained from various memories of the long term memory, as explained in greater detail below.

The cognitive working center 716 together with the cognitive working display 707 may be thought of as an inner voice and an inner eye in a human's mind. The cognitive working center 716 plans and generates conscious insights and/or thoughts and stores them to the long term memory 730 for later retrieval and for processing future thoughts. It also can share the conscious insights and/or thoughts via network 702 with other friends via social media, internet, and the like.

As shown in FIG. 7, the cognitive working center 716 receives a generated cognitive sensory memory or module and sends it to be displayed on the cognitive working display 707. User will review the cognitive sensory module displayed on the cognitive working display 707 and generate emotions, which are then processed into emotional information (EI) by the emotion information generator 70. The cognitive working center 716 parses the emotional information (EI) to determine various types of the emotions experienced by the user in response to the received sensory information (VI and AI), as shown in FIG. 8.

By way of an example, the cognitive working center 716 uses image recognition techniques, known in the art or later developed, to extract objects in the visual information and uses voice to text conversion techniques, known in the art or later developed, to extract more detailed specifications of objects being embodied in the VI and AI. The cognitive working center 716 then stores the classified VI and AI and EI with the determined type of the emotional signal in one of the areas of the long-term memory. For example, if the cognitive working center 716 determines that the EI has high values at ET01, ET02, ET09, and ET10 in which ET01 is highest, the cognitive sensory module (VI, AI, and E) will be stored in the semantic domain 726 MD01 in the long-term memory MD1 under the category LOVE (as shown in FIG. 8).

As shown in FIG. 7, the long term memory 730 (MD1 in FIG. 8) may include an episodic area 724 which stores episodic memories including a corresponding emotion invoked by the user in response to the VI and AI information. Episodic area 724 stores events and personal experiences including the emotions they invoked for the user. That is, in an exemplary embodiment, the episodic memory includes all memories (ones that may also be saved in semantic area) but these memories are stored in a chronological order. For example, the user may retrieve information about last year's annual meeting from this episodic area 724.

In an exemplary embodiment, cognitive working display 707 displays VI and AI retrieved from a cognitive sensory memory 740, by way of an example, or from the registering memory 712. However, the information displayed on a display 707 may be different from the information he was watching and listening to in class. At home, the user may review the same VI and AI obtained in class on the display 707 and may build more correlations with user's insights e.g., deeper understanding and/or higher confidence level, based on reviewing the semantic or topic. In an exemplary embodiment, based on at least the confidence emotion being at high level, the cognitive working center 716 may enable the system to save the cognitive sensory module to the long term memory. If both confidence and evident emotions are low while the center 716 need to work with other urgent tasks, the cognitive information is saved to uncompleted working memory 714 for further retrieval and processing when the working memory finish the urgent tasks.

By way of another example, if the user studies a simple semantic with domain MD01→MD06, such as, a police (MD02—people), pizza (MD03—food), a car (MD04—thing), elephant (MD05—animal), tree (MD06—botany), rain (MD07—phenomena), eating (MD08—processes) . . . , as shown in FIG. 8, the learned cognitive sematic is stored to its respective domain with the highest favorite (most liked item) being in on top in the respective domain. When the user searches the domain (his long term memory), a menu screen is provided to the user via the display 707, with eight icons for MD01→MD08. If he think about food, he will select icon MD03 then the semantic of chocolate (if he like chocolate most) will appear. This is provided by way of an example only and not by way of a limitation. In an exemplary embodiment, the user may retrieve his or her most favorite foods, people, and so on from various domains of a long term memory.

By way of another example, if a user studies a complex semantic. It is considered a thought and is related to an emotion on its importance or benefits. For example, when the user finishes the design of a new process, or a new business plan, it will be a complex completed thought with all ET09 (confident), ET10 (evident), and ET11 (desirous) being at their high levels. However, the design (or the plan) made the user feel very desirous by its promising usefulness in the recent market, user's emotion ET11 has the highest value in comparison with ET9, ET10 (he is also very confident and evident with the design (or the plan) but his desirous emotion, his hope is at the highest level in 3 types of the above emotions), this though may be saved on domain MD11—domain of desirous thoughts. Usually, these types of thoughts are named "Hopes", "Beliefs", and "Desires" of an individual. They are usually in a top of our mind.

Explorative emotions are from human's instincts. In an exemplary embodiment, if the student studied ten concepts, the cognitive working center 716 may save these concepts to thoughts area 728, with concepts that the user knows best to the top of MD09 and with concepts which appears to be most difficult, most bothersome, the ones with the highest risk of failure at examination, to the top of the domain MD12. The concepts are classified based on user's emotional state as measured by the sensors such as sensors S1-S16. Thoughts area 728 defines various thoughts of the user.

The semantic area 726 of the long-term memory 730 may define people MD02, food MD03, things MD04, and so on. For example, the semantic memory area for things MD04 may be divided into a number of sub-domains such as clothing, housing, and so on. In each domain, favorite sub-domains are on top when the user searches the domain. Such that when the user select "MD04" icon on menu, car, housing, golf icons will appear on menu screen, for example.

The long term memory 730 may be logically portioned into various areas, by way of an example and not by way of a limitation. Portioning may be physical or separate memories may be used to imitate various areas of the memory in a human's mind.

The cognitive working processor 711 also includes a scheduled memory 720. The scheduled memory 720 may store certain topics that are completed then to be executed by the cognitive working center 716 at a predetermined time. For example, the user may save the preparation for 8 am, Monday meeting, or the 10 am, Tuesday submitting sales contract in the scheduled memory 720. After being executed at the predetermined time, these topics will be stored in the long term memory 730 as normal completed topics. Accordingly, in an exemplary embodiment, the completed topic or thought in the cognitive working memory 718 maybe moved to the scheduled memory 720 instead of long-term memory 730 if it embodies as a set of schedule notes.

Figure 9:
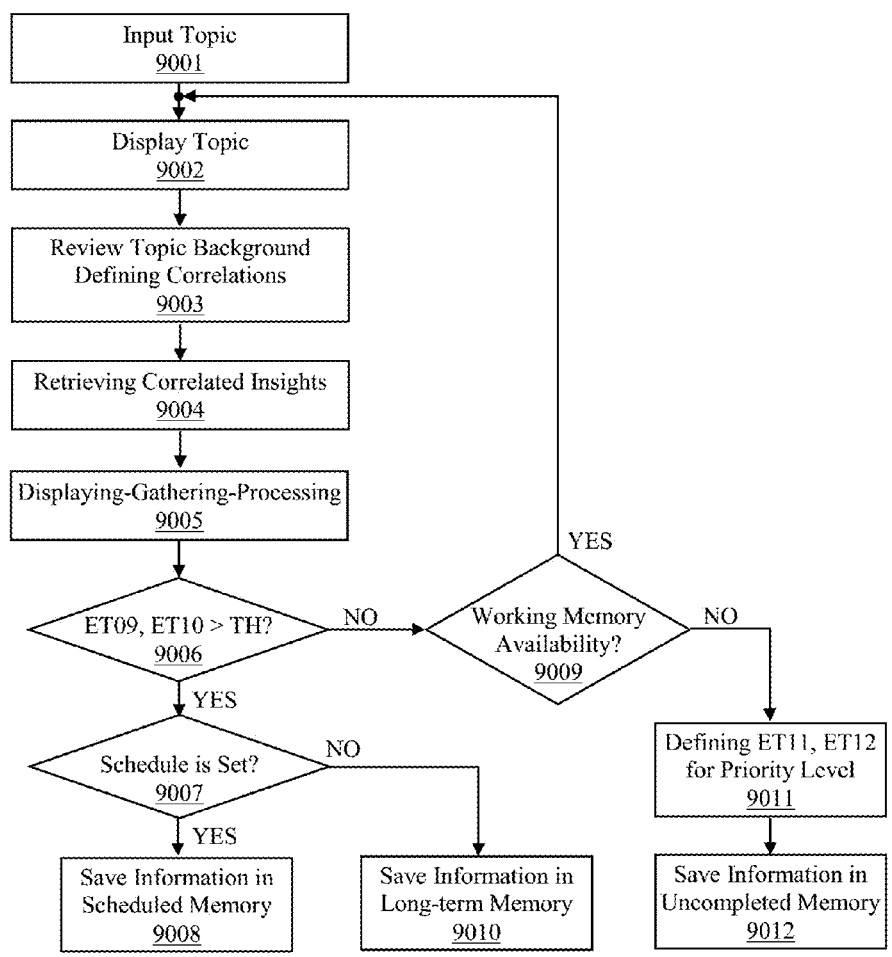
FIG. 9 is a flow chart illustrating a method of processing a cognitive module according to an exemplary embodiment.

FIG. 9 is a flowchart illustrating a method of producing cognitive insights according to an exemplary embodiment.

In an example embodiment, the user may select a topic in operation 9001. In operation 9002, the topic may be displayed by a cognitive working display in operation 9002. The user reviews the topic background and correlations are defined in operation 9003. Correlations may include two fingers, two parents if the input topic is 2. In operation 9004, correlated insights are retrieved from long-term memory and the retrieved correlation insights are displayed in operation 9005. While the user reviews the displayed topic, emotional information is generated based on user's emotional state e.g., user feels confident, evident, concerned, desirous, curious, etc. The obtained emotional information (EI) is compared with a reference state. By way of an example, if the discrimination between obtained ET09 and/or ET10 and the referenced samples are above a preset threshold value TH, in operation 9006, the system further checks in operation 9007 if a schedule is set in the cognitive module content. If no schedule is set, the information is saved in the long term memory, in operation 9010, for later retrieve. If a schedule is set, the information is saved in the scheduled memory for processing at a set time, in operation 9008.

Next, if both, discrimination between ET09 and ET10 and the referenced samples are below a threshold value, e.g. user has not yet understood the topic, need more thinking time, obtain more correlations, evidences to be more confident, e.g., the topic needs more processing, the system checks if the working memory is available, in operation 9009. If the working memory is available in operation 9009, the system returns the uncompleted topic to the operation 9002 for displaying and further processing until the topic is understood and completed. On the other hand, if working memory is not available, in operation 9009, the ET11 and ET12 values are defined for the important level and are saved in the uncompleted memory for later processing.

By way of another example, the user may request to review his or her shopping experience by retrieving all shopping items that she liked. The user may transfer the sensory memory to a cognitive insights producer such as the cognitive insights producer 700 illustrated in FIG. 7 (CIP). The CIP store the received sensory memory in the registering memory in a chronological order. Then the processor 711 can re-list in ET04 value order. The user will have a list of supervised things with the most favorite items appearing on top of the list (from most favorite to the least favorite based on the value of emotion ET04 that objects generated).

According to various exemplary embodiment, the cognitive module processor may function as an improved, individual, human mind. Based on the reference memories stored in the long term memory storage along with corresponding emotional information, the cognitive module processor may output alarms such as "don't eat this, you don't like broccoli" or output cognitive insights for the user such as "This is John, you like to watch basketball with John in sports café A". Also, the cognitive module processor may execute certain actions based on the received sensory data. For example, the cognitive module processor may send signal to call 911 if it determines (with high fear emotion level) that the user is in a car accident. The cognitive module processor may generate a text message to Ann if it determines that the user misses Ann and so on.

The descriptions of the various exemplary embodiments have been presented for purposes of illustration, but are not intended to be exhaustive or limited to the embodiments disclosed.

Many changes may be apparent to those of ordinary skill in the art without departing from the scope and spirit of the described embodiments. The terminology used herein was chosen to best explain the principles of the embodiments, the practical application or technical improvement over technologies found in the market place or to enable ordinary skill in the art to understand the embodiments disclosed herein.

In an exemplary embodiment, the cognitive module processor may be implemented on a tangible computer-readable medium. The term "computer-readable medium" as used herein refers to any medium that participates in providing instructions to a processor for execution. A computer readable medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable medium would include the following: an electrical connection having two or more wires, a portable computer diskette such as a floppy disk or a flexible disk, magnetic tape or any other magnetic medium, a hard disk., a random access memory (RAM), a read-only memory (ROM), an erasable programmable read-only memory (EPROM or Flash memory), a memory card, any other memory chip or cartridge, an optical fiber, a portable compact disc read-only memory (CD-ROM), any other optical medium, punchcards, papertape, any other physical medium with patterns of holes, or any other medium from which a computer can read or suitable combination of the foregoing.

In the context of this document, a computer readable medium may be any tangible, non-transitory medium that can contain, or store a program for use by or in connection with an instruction execution system, apparatus, or device.

Another form is signal medium and may include a propagated data signal with computer readable program code embodied therein, for example, in a base band or as part of a carrier wave. Such a propagated signal may take any of a variety of forms, including, but not limited to, the electro-magnetic, optical, or any suitable combination thereof. The signal medium may include coaxial cables, copper wire and fiber optics, including the wires that comprise data bus. The signal medium may be any medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire line, optical fiber cable, RF, etc. or any suitable combination of the foregoing.

Computer program code for carrying out operations for aspects of the exemplary embodiments may be written in any combination of one or more programming languages, including an object oriented programming language such as Java, Smalltalk, C++, .Net or the like and conventional procedural programming languages. The program code may execute entirely on the user's computer, partly on the user's computer, as a stand-alone software package, partly on the user's computer and partly on a remote computer or entirely on the remote computer or server. The remote computer may be connected to the user's computer through any type of network, including a local area network (LAN) or a wide area network (WAN), or the connection may be made to an external computer (for example, through the Internet using an Internet Service Provider).

The computer-readable medium is just one example of a machine-readable medium, which may carry instructions for implementing any of the methods and/or techniques described herein. Such a medium may take many forms, including but not limited to, non-volatile media and volatile media. Non-volatile media includes, for example, optical or magnetic disks. Volatile media includes dynamic memory.

Various forms of computer readable media may be involved in carrying one or more sequences of one or more instructions to a processor such as a CPU for execution. For example, the instructions may initially be carried on a magnetic disk from a remote computer. Alternatively, a remote computer can load the instructions into its dynamic memory and send the instructions over a telephone line using a modem. A modem local to a computer system can receive the data on the telephone line and use an infra-red transmitter to convert the data to an infra-red signal. An infra-red detector can receive the data carried in the infra-red signal and appropriate circuitry can place the data on the data bus. The bus carries the data to the volatile storage, from which processor retrieves and executes the instructions. The instructions received by the volatile memory may optionally be stored on persistent storage device either before or after execution by a processor. The instructions may also be downloaded into the computer platform via Internet using a variety of network data communication protocols well known in the art.

The flowchart and block diagrams in the Figures illustrate the architecture, functionality, and operation of possible implementations of systems, methods and computer program products according to various exemplary embodiments. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or two blocks may sometimes be executed in the reverse order, depending upon the functionality involved. It will also be noted that each block of the block diagram and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology as used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or acts for performing the function in combination with other claimed elements as specifically claimed.

The description of the exemplary embodiments has been presented for purposes of illustration and description, but is not intended to be exhaustive or limiting in any form. Many modifications and variations will be apparent to those of ordinary skill in the art without departing from the scope and spirit of the invention. Exemplary embodiments were chosen and described in order to explain operations and the practical applications thereof, and to enable others of ordinary skill in the art to understand various embodiments with various modifications as are suited to the particular use contemplated. That is, various modifications to these embodiments will be readily apparent to those skilled in the art, and the generic principles and specific examples defined herein may be applied to other embodiments without the use of inventive faculty. For example, some or all of the features of the different embodiments discussed above may be combined into a single embodiment. Conversely, some of the features of a single embodiment discussed above may be deleted from the embodiment. Therefore, the present disclosure is not intended to be limited to exemplary embodiments described herein but is to be accorded the widest scope as defined by the features of the claims and equivalents thereof.

What is claimed is:

1. A personal emotion-based cognitive assistant system comprising:
    at least one mechanism configured to capture, in real time, data about an environment comprising synchronized visual and audio information observed by a user;
    at least one sensor configured to capture an emotional state of the user corresponding to the captured synchronized visual and audio information;
    a processor configured to identify personal meaning of the environment of the user based on the captured emotional state; and
    a memory configured to store the identified personalized meaning with data about the environment in different areas of the memory based on the identified personal meaning,
    wherein the identifying of the personal meaning of the environment by the processor comprises:
        filter, detect, and identify instinct emotional signals of the user towards the stored captured synchronized visual and audio information based on the captured emotional state of the user and distinctive instinct reference signals stored in a database;
        identify the personal meaning of the environment, which is an instinct emotional code based on the identified corresponding instinct emotional signals, wherein the identified corresponding instinct emotional code embodies distinctive identified discriminations between components of the identified corresponding instinct emotional signals and the distinctive instinct reference signals, and
        generate a cognitive module by synthesizing the identified corresponding instinct emotional code with the corresponding stored captured synchronized visual and audio information,
    wherein the different areas of the memory are logically partitioned such that the different areas correspond to the distinctive instinct reference signals, which represent distinctive domains of a human instinct memory.

2. The personal emotion-based cognitive assistant of claim 1, further comprising an outputter configured to output results based on the personalized meaning of the data,
    wherein the outputter comprises:
        a working memory to store the results, and
        a display which is configured to output results stored in the working memory in forms of visual and audio information via at least one display screen and audio speakers,
    wherein the visual and audio information displayed by the outputter are the synchronized visual and audio information observed by the user with the corresponding instinct emotional signals,
    wherein the personalized meaning of the data is the identified instinct emotional code based on the identified corresponding instinct emotional signals,
    wherein the said results in the working memory comprise at least corresponding cognitive modules retrieved from insight memory,
    wherein the distinctive domains of a human instinct memory comprise a reproductive domain, a survival domain, and an explorative domain, and
    wherein, in response to identifying another corresponding instinct emotional code of the user for newly captured information, the processor is further configured to retrieve the stored cognitive modules in the memory in corresponding to said another corresponding instinct emotional code and store said newly captured information in the working memory.

3. The personal emotion-based cognitive assistant of claim 1,
    wherein the at least one mechanism configured to capture, in real time, the synchronized visual and audio information observed by the user; comprises at least one camera and at least one microphone,
    wherein the distinctive instinct reference signals are explorative instinct reference signals, and
    wherein the generated cognitive module is stored in sensory areas of the memory.

4. The personal emotion-based cognitive assistant of claim 2, further comprising: an output mechanism, which is configured to output via a speaker and a display working visual and audio information,
    wherein the synchronized visual and audio information observed by the user is the working visual and audio information,
    wherein the at least one mechanism configured to capture, in real time, the synchronized visual and audio information observed by the user is the working memory which is storing the working visual and audio information displayed on the output mechanism.

5. The personal emotion-based cognitive assistant of claim 1, wherein:
    the at least one sensor comprises a plurality of sensors measuring activity in a head of the user to output a plurality of brain wave signals,
    the processor filters, detects, identifies instinct emotional information from the plurality of brain wave signals based on the distinctive referenced instinct signals, generates the composite instinct emotional information, compares the generated composite instinct emotional information with the distinctive referenced instinct signals to control the memory to store the data based on the comparison.

6. The personal emotion-based cognitive assistant of claim 3, wherein:
    the at least one sensor comprises a plurality of sensors configured to sense multi-emotion signals of the user,
    the processor is further configured to process the multi-emotion signals to generate emotion information and determine whether the generated emotion information is above a threshold value indicating that a user is paying attention to the captured visual and audio data, and
    in response to the determining that the emotion information is above the threshold value, forming and storing in the memory, the generated cognitive module,
    wherein the cognitive module is stored in the sensory memory area from among the different areas of the memory.

7. The personal emotion-based cognitive assistant system of claim 6, further comprising:
    a buffer configured to store the captured synchronized visual and audio information for a period of time corresponding to a period of time prior to the human brain issuing an instinct emotional code.

8. The personal emotion-based cognitive assistant system of claim 3, wherein the system is a headset worn by a user providing sensory cognitive memory when the user observes the synchronized visual and audio information and providing the instinct emotional signals for the system when the user observes a display of the output mechanism.

9. The personal emotion-based cognitive assistant system of claim 4, wherein:

the processor is further configured to determine whether the captured emotional state is above another threshold value indicating that the user is confident or evident with the working visual and audio information displayed on the output mechanism, in response to the processor determining that the captured emotional state is above said another threshold value, forming the cognitive module comprising the instinct emotional code generated based on the captured emotional state together with the corresponding displayed working visual and audio information and storing the formed cognitive module in the long term memory area from among the distinct areas of the memory.

10. The personal emotion-based cognitive assistant system of claim 9, wherein:
the long term memory area comprises a plurality of sub-areas,
the plurality of sub-areas of the long term memory area comprise an episodic sub-area, a semantic sub-area, a thoughts sub-area, and an instincts sub-area, and
the processor is further configured to determine, based on the captured emotional state of the user, at least one of the plurality of sub-areas to store the generated cognitive module.

11. The emotion-based cognitive assistant system of claim 4, wherein the at least one sensor comprises a plurality of sensors, which are positioned at different locations on the user and wherein the plurality of sensors comprise a first sensor dedicated to detect a reproductive instinct of the user, a second sensor dedicated to detect a survival instinct of the user, and a third sensor dedicated to detect an explorative instinct of the user.

12. The emotion-based cognitive assistant system of claim 11, wherein the processor is configured to classify a plurality of different types of emotions captured by the plurality of sensors into at least one of a reproductive instinct, a survival instinct, and an explorative instinct such that an area from among the distinct areas is identified based on a composite emotions generated from outputs of the plurality of sensors.

13. The emotion-based cognitive assistant system of claim 12, further comprising a touch screen and a sketchpad on the display configured to input manually at least one of further details, modifications, text, and sketches, to move, zoom, edit directly onto visual information of working cognitive modules.

14. The emotion-based cognitive assistant system of claim 13, wherein the display is further configured to output emotion information component of the plurality of working cognitive modules in different forms comprising at least one of: sounds, toolbars, locations, and color coding of graphical user interface elements.

15. The emotion-based cognitive assistant system of claim 14, wherein the memory is further divided into the distinct areas, which comprise a registering memory area which stores the interface memory, a working memory area which mimic the thinking in the human mind, an uncompleted working memory area which store unsolved problems, a scheduled memory area which stores future time-defined plans and executions, and a long-term memory area which corresponds to the long term memory of the human mind.

16. The emotion-based cognitive assistant system of claim 15, wherein the working memory stores information in process of being verified, modified, added, combined, edited, and displayed on the output mechanism, wherein the registering memory stores at least one of input information waiting for processing in the working memory, the uncompleted working memory stores interrupted working information modules when the working memory is busy with a cognitive module having a higher importance, and the scheduled memory stores cognitive information modules embodying specific scheduled notes.

17. The emotion-based cognitive assistant system of claim 16, wherein the long-term memory comprises:
an episodic memory storing verified cognitive information modules in a chronological order,
a semantic memory storing the verified cognitive information modules organized by categories, wherein the categories represent distinctive domains of an instinct emotional coding system,
a thoughts memory storing completed cognitive working information modules in an order of importance, and
a personal instinct referenced memory storing distinctive instinct referenced signals.

18. The personal emotion-based cognitive assistant of claim 8, further comprising:
a display which displays visual and audio data,
wherein the processor is further configured to identify personal meaning of said displayed visual and audio data and in response to the identified personal meaning, to retrieve correlated cognitive information from the memory,
wherein the display is further configured to further display the retrieved correlated cognitive information, and
wherein the processor is further configured to gather, verify, and process the displayed output cognitive information, and in response to the cognitive information being verified, controlling the memory to store the results in one of the plurality of distinct memory areas.

19. A method of providing personal emotion-based cognitive assistance comprising:
capturing, in real time, by at least one mechanism, data about an environment comprising synchronized visual and audio information observed by a user;
capturing, by at least one sensor, emotional state of the user corresponding to the captured synchronized visual and audio information;
identifying, by a processor, personal meaning of the environment of the user based on the captured emotional state;
storing, in a memory, the identified personalized meaning with data about the environment in different areas of the memory based on the identified personal meaning,
wherein the identifying of the personal meaning of the environment by the processor comprises:
filtering, detecting, and identifying instinct emotional signals of the user towards the stored captured synchronized visual and audio information based on the captured emotional state of the user and distinctive instinct reference signals stored in a database;
identifying the personal meaning of the environment, which is an instinct emotional code based on the identified corresponding instinct emotional signals, wherein the identified corresponding instinct emotional code embodies distinctive identified discriminations between components of the identified corresponding instinct emotional signals and the distinctive instinct reference signals;
generating a cognitive module by synthesizing the identified corresponding instinct emotional code with the corresponding stored captured synchronized visual and audio information;

wherein the different areas in the memory are logically partitioned such that the different areas correspond to the distinctive instinct reference signals, which represent distinctive domains of a human instinct memory.

20. The method of claim 19, further comprising displaying, on a display, the generated cognitive module and messages indicating comfort level of the user with respect to the captured video and audio data.

21. The method of claim 19, further comprising:
inputting, on a display which functions as a sketchpad, at least one of details, modifications, text, and sketches; and
inputting, on the display which functions as a touch screen, at least one of a moving command, a zooming command, and an editing command with respect to the input details.

22. A non-transitory computer readable medium configured to store instructions, which when executed by the processor cause the processor to execute the following operations:
receiving, in real time, data about an environment comprising synchronized visual and audio information observed by a user;
receiving an emotional state of the user, captured by at least one sensor, corresponding to the captured synchronized visual and audio information;
identifying personal meaning of the environment of the user based on the captured emotional state;
storing the identified personalized meaning with data about the environment in different areas of the memory based on the identified personal meaning,
wherein the identifying of the personal meaning of the environment comprises:
filtering, detecting, and identifying instinct emotional signals of the user towards the stored captured synchronized visual and audio information based on the captured emotional state of the user and distinctive instinct reference signals stored in a database;
identifying the personal meaning of the environment, which is an instinct emotional code based on the identified corresponding instinct emotional signals, wherein the identified corresponding instinct emotional code embodied distinctive identified discriminations between components of the identified corresponding instinct emotional signals and the distinctive instinct reference signals, and
generate a cognitive module by synthesizing the identified corresponding instinct emotional code with the corresponding stored captured synchronized visual and audio information,
wherein the different areas of the memory are logically partitioned such that the different areas correspond to the distinctive instinct reference signals, which represent distinctive domains of a human instinct memory.

* * * * *